United States Patent
Byrum et al.

(10) Patent No.: US 7,951,067 B2
(45) Date of Patent: May 31, 2011

(54) IMPLANTABLE BAND HAVING IMPROVED ATTACHMENT MECHANISM

(75) Inventors: Randal T. Byrum, Milford, OH (US); Kristin L. Jambor, Cincinnati, OH (US); Thomas E. Albrecht, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1143 days.

(21) Appl. No.: 10/742,483

(22) Filed: Dec. 19, 2003

(65) Prior Publication Data

US 2004/0267288 A1    Dec. 30, 2004

Related U.S. Application Data

(60) Provisional application No. 60/483,353, filed on Jun. 27, 2003, provisional application No. 60/507,625, filed on Sep. 30, 2003.

(51) Int. Cl.
*A61F 2/00* (2006.01)

(52) U.S. Cl. ............ 600/37; 606/151; 606/157; 24/466; 24/474

(58) Field of Classification Search ............ 606/151, 606/157; 24/163 R, 164–200, 461, 466, 24/467, 469, 474, 477, 478, 485, 542; 600/31, 600/37

See application file for complete search history.

(56) References Cited

U.S. PATENT DOCUMENTS

| | | | |
|---|---|---|---|
| 771,586 A | 10/1904 | Stiles | |
| 2,637,887 A | 5/1953 | Goodman et al. | |
| 3,080,635 A | 3/1963 | Gunther et al. | |
| 3,181,189 A | 5/1965 | Leyden | |
| 3,214,808 A | 11/1965 | Litwin | |
| 3,576,054 A | 4/1971 | Rynk | |
| 3,605,726 A | 9/1971 | Williams et al. | |
| 3,726,279 A | 4/1973 | Barefoot et al. | |
| 3,860,997 A | 1/1975 | Van Riper, Jr. et al. | |
| 4,037,603 A * | 7/1977 | Wendorff | 606/157 |
| 4,150,464 A | 4/1979 | Tracy | |
| 4,154,418 A | 5/1979 | Wiese | |
| 4,458,395 A | 7/1984 | Aoki | |
| 4,478,219 A | 10/1984 | Rozario et al. | |
| 4,532,868 A | 8/1985 | Gleichaut et al. | |
| 4,538,304 A | 9/1985 | Grafelmann | |
| 4,592,339 A | 6/1986 | Kuzmak et al. | |
| 4,592,355 A | 6/1986 | Antebi | |
| 4,688,337 A | 8/1987 | Dillner et al. | |
| 4,706,914 A | 11/1987 | Ground | |
| 4,779,314 A | 10/1988 | Aoki | |

(Continued)

FOREIGN PATENT DOCUMENTS

EP    0 611 561 A1    9/1993

(Continued)

OTHER PUBLICATIONS

Office Action dated Dec. 15, 2004 for U.S. Appl. No. 10/677,088, filed Sep. 30, 2003.

(Continued)

*Primary Examiner* — Todd E Manahan
*Assistant Examiner* — Michael G Mendoza

(57) ABSTRACT

An implantable band for placement around an anatomical passageway, such as the stomach or other lumen, includes a first end portion with an opening configured to receive part of a second end portion, with a retaining part included as part of the first or second end portion.

9 Claims, 13 Drawing Sheets

U.S. PATENT DOCUMENTS

| | | | |
|---|---|---|---|
| 4,854,014 A | 8/1989 | Ueno | |
| 4,907,513 A | 3/1990 | Manion et al. | |
| 5,028,027 A | 7/1991 | Fraser | |
| D319,311 S | 8/1991 | Kohler | |
| 5,074,868 A | 12/1991 | Kuzmak | |
| 5,152,770 A | 10/1992 | Bengmark et al. | |
| 5,160,338 A | 11/1992 | Vincent | |
| 5,226,429 A | 7/1993 | Kuzmak | |
| 5,249,338 A | 10/1993 | Aoki | |
| 5,274,889 A | 1/1994 | Morit | |
| 5,363,536 A | 11/1994 | Kleemann | |
| 5,449,368 A | 9/1995 | Kuzmak | |
| 5,522,529 A | 6/1996 | Yurman et al. | |
| 5,527,355 A | 6/1996 | Ahn | |
| 5,584,452 A | 12/1996 | Koike | |
| 5,601,604 A * | 2/1997 | Vincent | 606/216 |
| 5,604,604 A | 2/1997 | Fan | |
| 5,683,404 A | 11/1997 | Johnson | |
| 5,707,378 A | 1/1998 | Ahn et al. | |
| 5,810,845 A | 9/1998 | Yoon | |
| 5,843,170 A | 12/1998 | Ahn | |
| 5,843,179 A | 12/1998 | Ahn | |
| 5,868,140 A | 2/1999 | Miller et al. | |
| RE36,176 E | 3/1999 | Kuzmak | |
| 6,461,292 B1 | 10/2002 | Forsell | |
| 6,470,892 B1 | 10/2002 | Forsell | |
| 6,511,490 B2 * | 1/2003 | Robert | 606/151 |
| 6,782,572 B1 | 8/2004 | Jones | |
| 2002/0087431 A1 | 7/2002 | Morishima | |
| 2002/0183768 A1 | 12/2002 | Deem et al. | |
| 2002/0198548 A1 | 12/2002 | Robert | |
| 2003/0105385 A1 | 6/2003 | Forsell | |
| 2003/0114729 A1 | 6/2003 | Forsell | |
| 2004/0230137 A1 | 11/2004 | Mouton | |
| 2004/0267291 A1 | 12/2004 | Byrum et al. | |
| 2004/0267292 A1 | 12/2004 | Byrum et al. | |
| 2005/0002984 A1 | 1/2005 | Byrum et al. | |
| 2005/0125014 A1 | 6/2005 | Duluco et al. | |

FOREIGN PATENT DOCUMENTS

| | | |
|---|---|---|
| EP | 0 611 561 B1 | 9/1993 |
| EP | 608 580 | 3/1994 |
| EP | 0 702 529 B1 | 5/1994 |
| EP | 1 205 148 A1 | 5/1994 |
| EP | 0 885 031 B1 | 6/1997 |
| EP | 0 923 356 B1 | 6/1998 |
| EP | 1 091 707 A1 | 6/1999 |
| EP | 1 036 545 A2 | 3/2000 |
| EP | 1 113 767 A0 | 3/2000 |
| EP | 1 198 211 A1 | 7/2000 |
| EP | 1 216 012 A1 | 9/2000 |
| EP | 1 237 486 A2 | 12/2000 |
| EP | 1 244 399 A 1 | 12/2000 |
| EP | 1 251 808 A1 | 1/2001 |
| EP | 1 259 170 A1 | 3/2001 |
| EP | 1 281 360 | 7/2002 |
| EP | 1281360 | 7/2002 |
| EP | 1 342 458 | 9/2003 |
| EP | 1 396 242 | 3/2004 |
| EP | 1 491 167 | 12/2004 |
| EP | 1 491 168 | 12/2004 |
| FR | 2434089 | 3/1980 |
| FR | 2 825 264 | 12/2002 |
| FR | 2825264 | 12/2002 |
| FR | 2 827 756 | 1/2003 |
| FR | 2827756 | 1/2003 |
| GB | 2 139 902 | 5/1984 |
| GB | 2 139 902 A | 5/1984 |
| JP | 08052147 | 8/1994 |
| JP | 09117454 A | 10/1995 |
| WO | WO 86/04498 | 8/1986 |
| WO | WO 87/00034 | 1/1987 |
| WO | WO 92/02182 | 2/1992 |
| WO | WO 92/21293 | 12/1992 |
| WO | WO 94/05214 | 3/1994 |
| WO | WO 94/27504 | 12/1994 |
| WO | WO 98/56321 | 12/1998 |
| WO | WO 99/34748 | 7/1999 |
| WO | WO 00/69376 | 11/2000 |
| WO | WO 01/10359 A1 | 2/2001 |
| WO | WO 01/19297 A1 | 3/2001 |
| WO | WO 01/24742 A1 | 4/2001 |
| WO | WO 01/41671 A2 | 6/2001 |
| WO | WO 01/45597 A1 | 6/2001 |
| WO | WO 01/52777 | 7/2001 |
| WO | WO 01/68007 A1 | 9/2001 |
| WO | WO 01/85071 A1 | 11/2001 |
| WO | WO 02/053040 A1 | 7/2002 |
| WO | WO 02/064041 A1 | 8/2002 |
| WO | WO 02/071951 A1 | 9/2002 |
| WO | WO 02/091961 A1 | 11/2002 |
| WO | WO 02/096326 A2 | 12/2002 |
| WO | WO 02/096327 A2 | 12/2002 |
| WO | WO 03/101352 | 12/2003 |
| WO | WO 2004/108025 | 12/2004 |

OTHER PUBLICATIONS

Amendment and Response dated Mar. 11, 2005 for U.S. Appl. No. 10/677,088, filed Sep. 30, 2003.
Office Action dated Oct. 19, 2004 for U.S. Appl. No. 10/676,368, filed Sep. 30, 2003.
Amendment and Response dated Feb. 18, 2005 for U.S. Appl. No. 10/676,368, filed Sep. 30, 2003.
Office Action dated May 11, 2005 for U.S. Appl. No. 10/676,368, filed Sep. 30, 2003.
US Patent Office Action dated Aug. 25, 2005, for U.S. Appl. No. 10/677,088, filed Sep. 30, 2003.
Amendment and Response to Office Action filed on Dec. 20, 2005 for U.S. Appl. No. 10/677,088, filed Sep. 30, 2003.
U.S. Appl. No. 60/483,353, filed Jun. 27, 2003, Byrum et al.
U.S. Appl. No. 60/507,612, filed Sep. 30, 2003, Byrum et al.
U.S. Appl. No. 60/507,625, filed Sep. 30, 2003, Byrum et al.
U.S. Appl. No. 60/507,916, filed Sep. 30, 2003, Byrum et al.
U.S. Appl. No. 10/676,368, filed Sep. 30, 2003, Byrum et al.
U.S. Appl. No. 10/677,088, filed Sep. 30, 2003, Byrum et al.
U.S. Appl. No. 10/741,869, filed Dec. 9, 2003, Byrum et al.
ESR dated Mar. 23, 2005 for Application No. EP 04256037.
EPO Communication dated Sep. 24, 2004 for Application No. EP 04253607.
Indian Search Report, Serial No. 357/KOL/2004, p. 1.
Notice of Allowance dated Jan. 2, 2008 for U.S. Appl. No. 10/741,869.
Notice of Allowance dated Mar. 17, 2008 for U.S. Appl. No. 10/741,869.
Notice of Allowance dated May 30, 2008 for U.S. Appl. No. 10/741,869.
Office Action dated Jun. 11, 2008 for U.S. Appl. No. 10/874,881.
Nonfinal Rejection dated Aug. 20, 2008 for U.S. Appl. No. 10/677,088.
European Search Report dated Sep. 16, 2004 for Application No. EP 04253607.
European Communication dated Oct. 15, 2007 for Application No. EP 04253607.
Australian Search Report dated Apr. 24, 2009 for Application No. 2004202898.
European Search Report dated Jan. 18, 2005 for EPO 04 25 6021.
Amendment dated Feb. 18, 2005 for U.S. Appl. No. 10/676,368.
Office Action dated Sep. 21, 2005 for U.S. Appl. No. 10/676,368.
Amendment and Response dated Mar. 11, 2005 for U.S. Appl. No. 10/677,088.
Office Action dated Aug. 25, 2005 for U.S. Appl. No. 10/677,088.
Amendment and Response dated Dec. 20, 2005 for U.S. Appl. No. 10/677,088.
Office Action dated May 8, 2007 for U.S. Appl. No. 10/677,088.
Notice of Allowance dated Sep. 25, 2007 for U.S. Appl. No. 10/677,088.
Office Action dated Sep. 8, 2006 for U.S. Appl. No. 10/741,869.
Office Action dated Jul. 11, 2007 for U.S. Appl. No. 10/741,869.

* cited by examiner

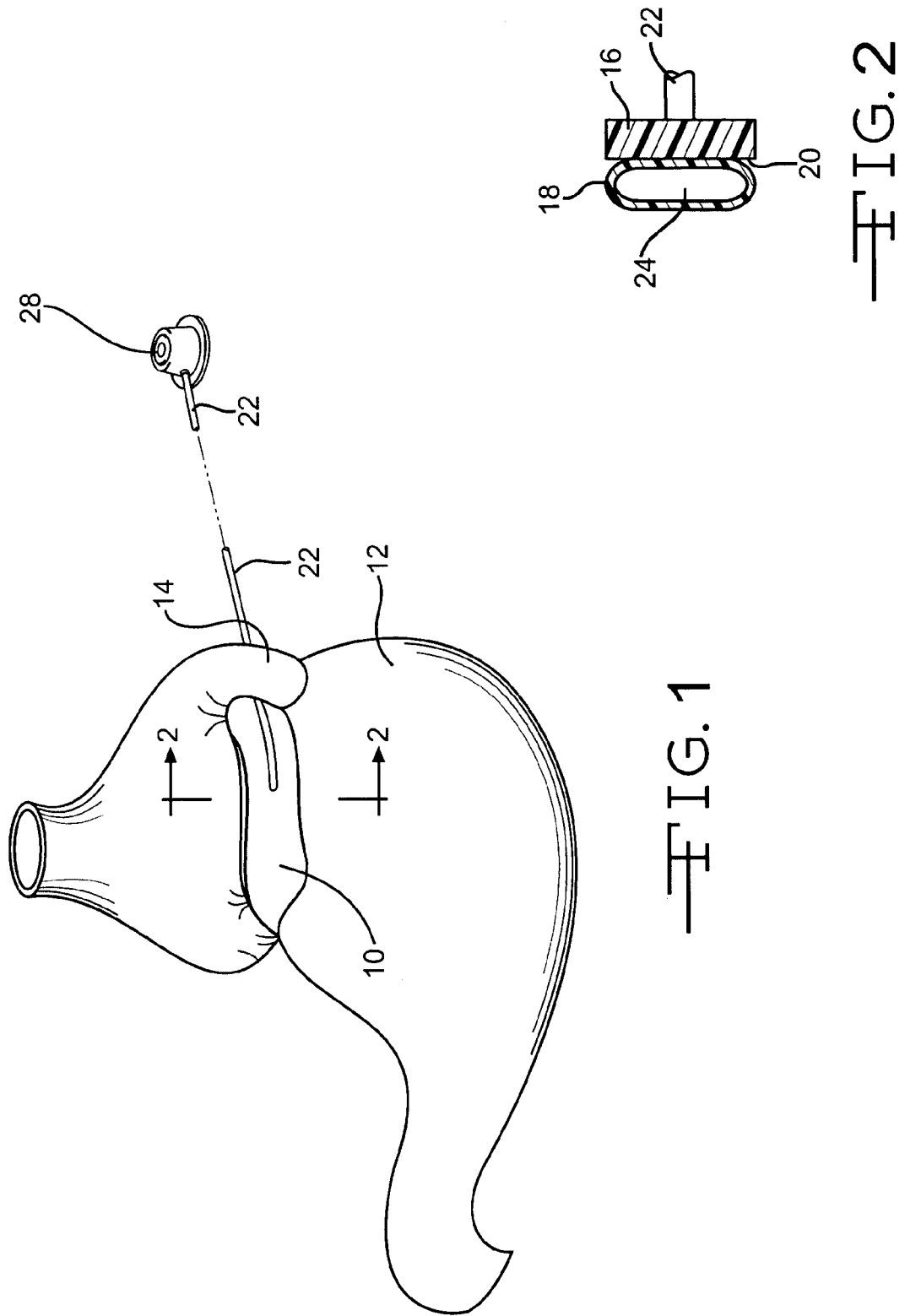

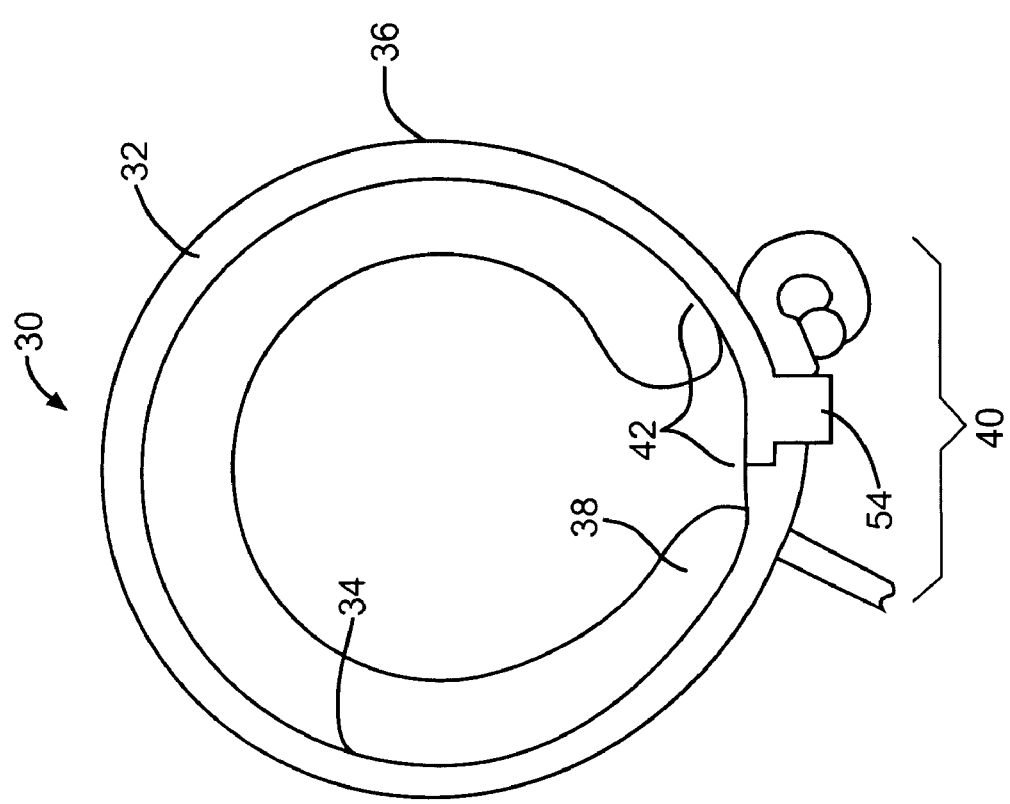

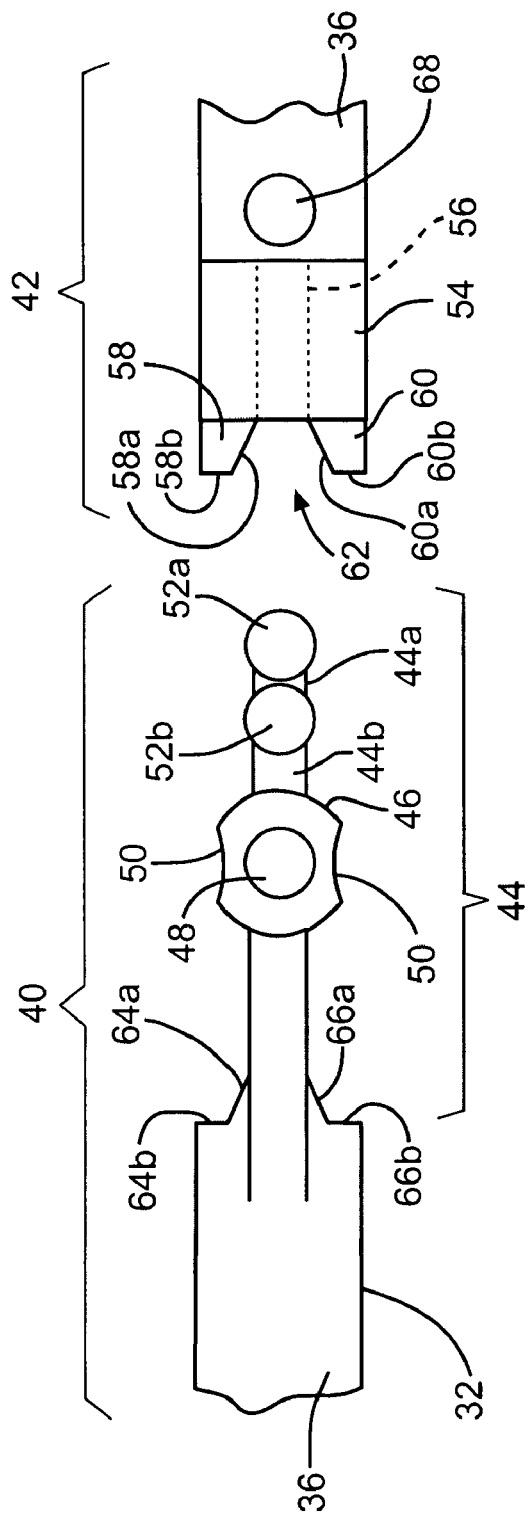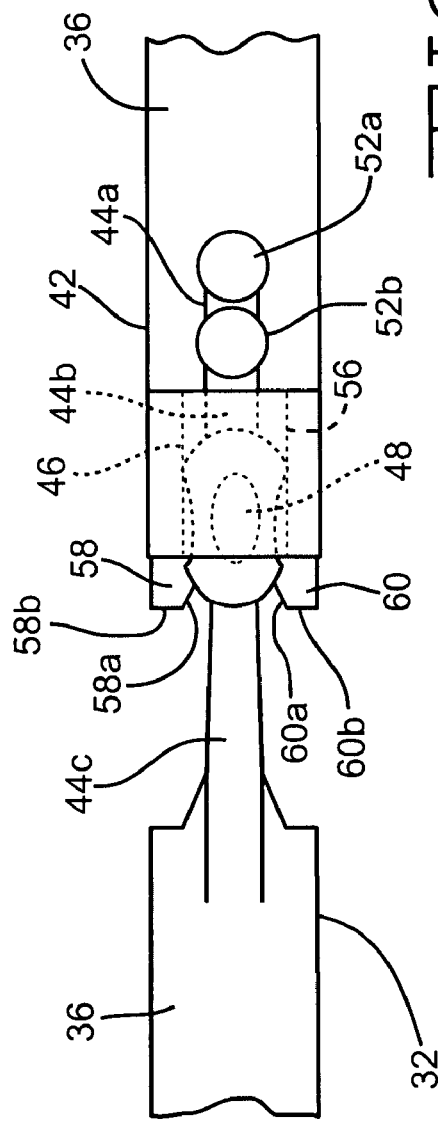
FIG. 4A
FIG. 4B

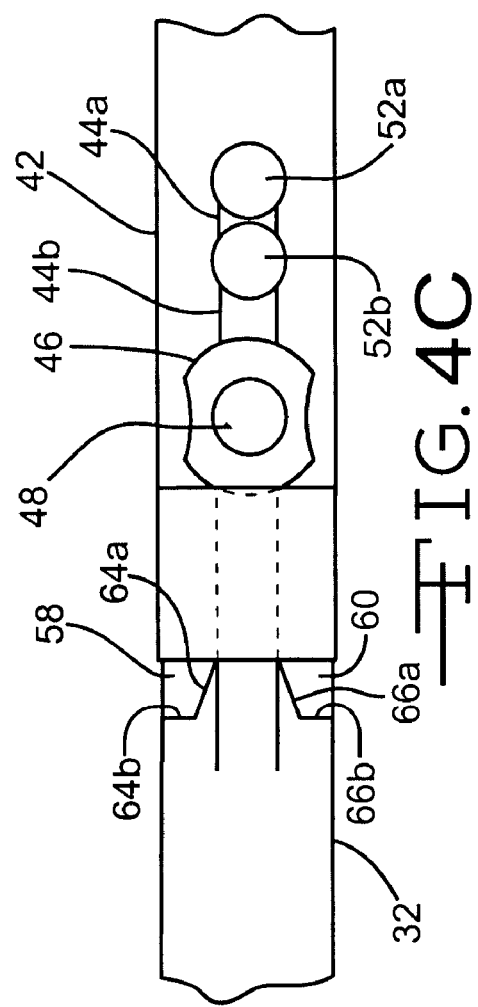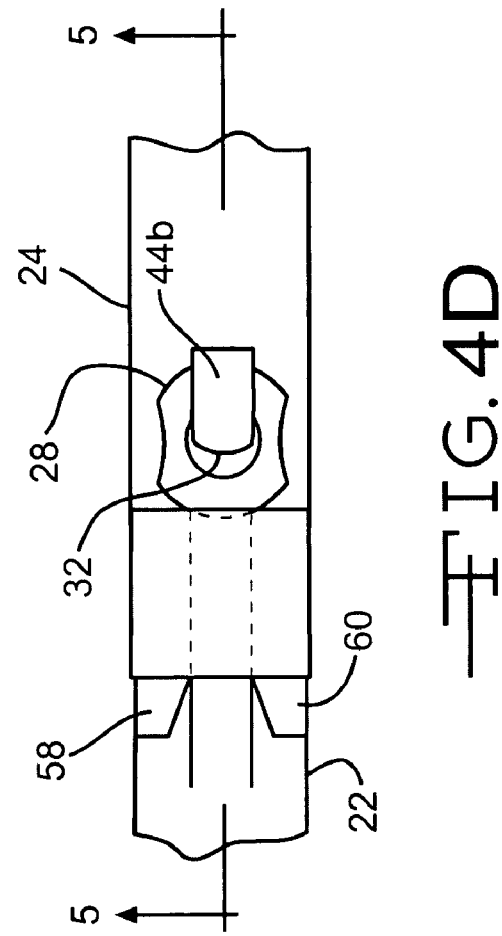

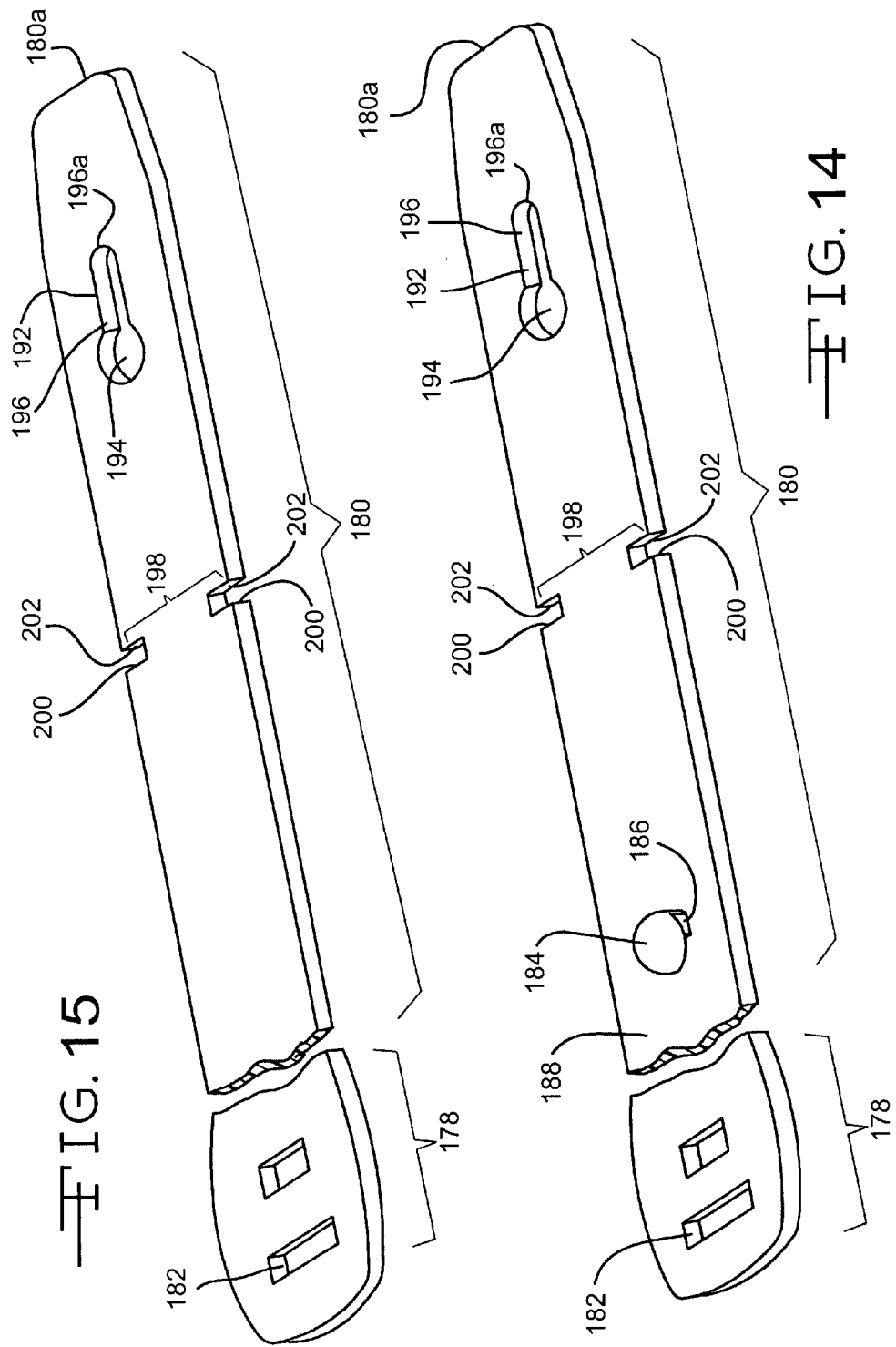

US 7,951,067 B2

IMPLANTABLE BAND HAVING IMPROVED ATTACHMENT MECHANISM

RELATED APPLICATIONS

This application claims priority from U.S. Provisional Patent Application Ser. No. 60/483,353, titled Adjustable Gastric Band Having An Improved Attachment Mechanism, filed on Jun. 27, 2003, and U.S. Provisional Patent Application Ser. No. 60/507,625, titled Implantable Band Having Improved Attachment Mechanism, filed on Sep. 30, 2003, the disclosures of both of which are incorporated herein by reference. This application also incorporates by reference co-pending U.S. Patent Application filed of even date herewith, application Ser. No. 10/742,483, titled Implantable Band With Attachment Mechanism, inventors Byrum, Jambor, Conlon, Crawford, Harper and Spreckelmeyer. This application also incorporates by reference the following co-pending U.S. patent applications filed on Sep. 30, 2003: application Ser. No. 10/677,088, titled Implantable Band with Transverse Attachment Mechanism, inventors: Byrum, Jambor and Crawford; application Ser. No. 10/676,368, titled Implantable Band with Non-Mechanical Attachment Mechanism, inventors: Byrum and Nuchols; Provisional Application Ser. No. 60/507,916, Implantable Band with Attachment Mechanism, inventors: Byrum, Jambor, Conlon, Crawford, Harper and, Spreckelmeier; and Provisional Application Ser. No. 60/507,916, Implantable Band with Deformable Attachment Mechanism, inventors: Byrum, Wiley, Conlon and Fender.

TECHNICAL FIELD

This present invention relates generally to a surgically implantable band for encircling an anatomical passageway, and is particularly directed to an adjustable gastric band for encircling the stomach for the control of obesity. The invention will be specifically disclosed in connection with an improved attachment mechanism for an adjustable gastric band.

BACKGROUND OF THE INVENTION

Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that is less than the normal interior diameter of the stomach that restricts food passing from an upper portion to a lower digestive portion of the stomach. When the stoma is of the appropriate size, food held in the upper portion of the stomach provides a feeling of fullness that discourages overeating.

In addition to a latched position to set the diameter of the gastric band, adjustability of gastric bands is generally achieved with an inwardly directed inflatable balloon, similar to a blood pressure cuff, into which fluid, such as saline, is injected through a fluid injection port to achieve a desired diameter. The balloon is typically deflated or only partially inflated when first placed in the body to allow for body adjustments and healing around the new band site. Since adjustable gastric bands may remain in the patient for long periods of time, the fluid injection port is typically installed subcutaneously to avoid infection, for instance in front of the sternum. Following the initial implantation, the surgeon may adjust the band by loosing or tightening depending on the patients' needs. Adjusting the amount of fluid in the adjustable gastric band is achieved by inserting a Huber tip needle through the skin into a silicone septum of the injection port. Once the needle is removed, the septum seals against the hole by virtue of compressive load generated by the septum. A flexible conduit communicates between the injection port and the adjustable gastric band.

An attachment mechanism for the adjustable gastric band has to provide an initial sizing of the stoma of the stomach. One generally known attachment is to suture ends of the adjustable gastric band. Another generally known attachment includes one end of the gastric band terminating in a flexible conduit that has a flared portion that is drawn through an opening in a second end of the gastric band and then sutured to the encircling band portion—securing the band to the stomach. After the sutures are in place, the injection port is anchored at a convenient location.

While these known approaches are effective in securing the gastric band, further improvements are desired that simplify the clinical implantation procedure, that provide long-term reliability, and that facilitate readjustment or removal.

While sutures have been relied on as the most positive connection in the past, it is desirable to have a secure attachment that does not require sutures, yet does not require a large force to create the secure attachment. Otherwise, it may be difficult to adequately grip and perform the attachment with laparoscopic instruments. Consequently, a significant need exists for an adjustable gastric band having an improvement attachment mechanism.

SUMMARY OF THE INVENTION

The present invention addresses these and other problems in the prior art, by providing an adjustable gastric band device that is engaged with less force, thereby facilitating implementation with laparoscopic instruments, yet the attachment remains secure over long term use.

A general object of this invention is to provide an adjustable gastric band where insertion of a second end into a first end requires a low amount of force, and a lock element is engaged so that a very high amount of force is required to separate the two ends.

Another object of this invention is to provide a readily reversible adjustable gastric band which can be fastened and unfastened without reducing the holding strength of the attachment mechanism.

Another object of this invention is to provide an adjustable gastric band having longitudinal forces that are transferred through the attachment mechanism that may be relatively large without causing detachment, while engagement forces are relatively low.

To achieve the foregoing and other objects, and in accordance with the purposes of the present invention as described herein, there are described adjustable gastric bands with opposing surface attachment mechanisms having a member extending laterally from one end which is configured to engage the other end. In accordance with one aspect, the lateral member includes a passageway which receives a portion of the other end. In another aspect, the lateral member is received by an opening in the other end.

In the present invention, an adjustable gastric band is provided with a two-step attachment mechanism that allows an initial attachment to confirm placement, followed by a second engagement to give a visual indication of a secure attachment and to add to the strength of the attachment.

Further novel features and other objects of the present invention will become apparent from the following detailed description, discussion and the appended claims, taken in conjunction with the drawings.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1 is a diagrammatic drawing showing an adjustable gastric band wrapped around an upper part of a stomach.

FIG. 2 is a cross sectional view of the adjustable gastric band of FIG. 1 taken along line 2-2.

FIG. 3 is a top view of an adjustable gastric band constructed in accordance with the present invention having an attachment mechanism which requires two steps to connect the two ends together.

FIGS. 4A-D are a sequence of fragmentary side views of the ends of the adjustable gastric band of FIG. 3, illustrating the steps in securing the ends together.

FIG. 7A is an enlarged, fragmentary perspective view taken along line 7A of FIG. 7.

FIG. 14 is an enlarged, fragmentary perspective view of the outer surface of the embodiment shown in FIG. 13, with the two end portions unengaged.

FIG. 15 is an enlarged, fragmentary perspective view of the inner surface of the embodiment shown in FIG. 13, with the two end portions unengaged.

Figure 5:
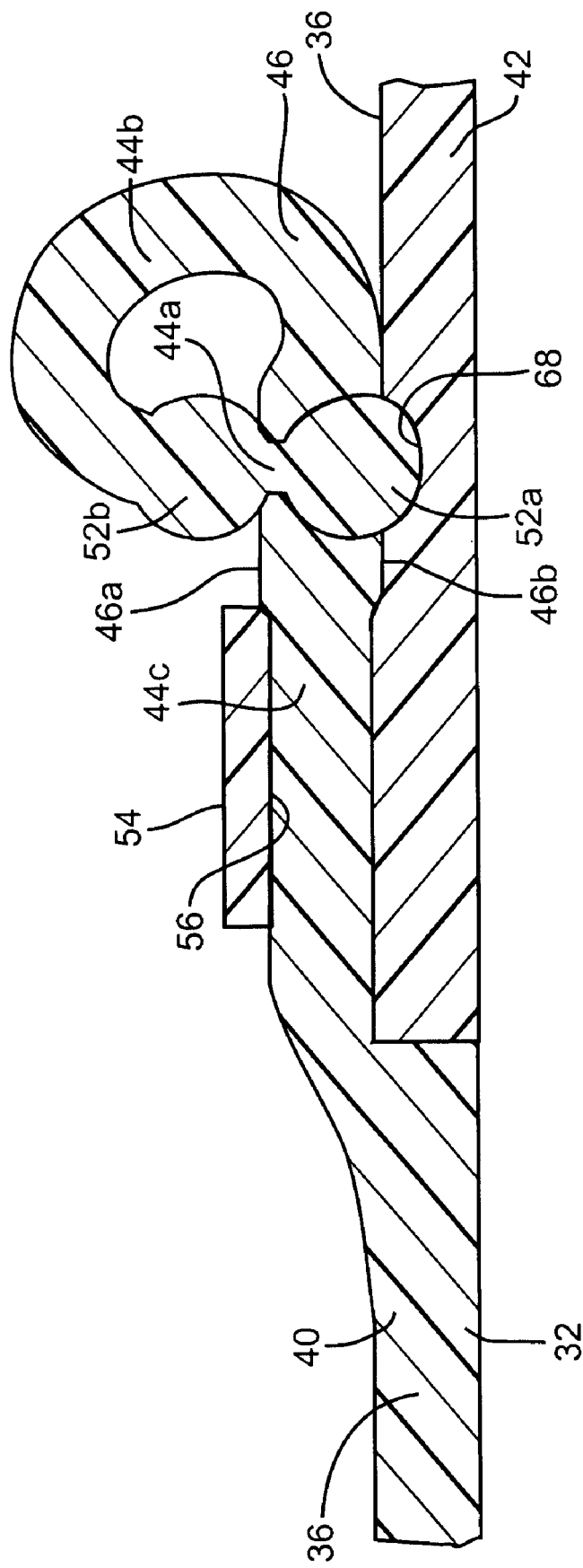
FIG. 5 is an enlarged, cross section side view of the adjustable gastric band of FIG. 3 taken along line 5-5 of FIG. 4D.

Reference will now be made in detail to the present preferred embodiment of the invention, an example of which is illustrated in the accompanying drawings.

DETAILED DESCRIPTION OF THE INVENTION

In the following description, like reference characters designate like or corresponding parts throughout the several views. Also, in the following description, it is to be understood that terms such as front, back, inside, outside, and the like are words of convenience and are not to be construed as limiting terms. Terminology used in this patent is not meant to be limiting insofar as devices described herein, or portions thereof, may be attached or utilized in other orientations. Referring in more detail to the drawings, the invention will now be described.

Referring to FIG. 1, an adjustable gastric band 10 is shown wrapped around an upper portion of a stomach 12, kept in place by attaching the two ends together and extending a portion 14 of the stomach 12 over the adjustable gastric band 10 by suturing portion 14 to the stomach. Referring also to FIG. 2, the adjustable gastric band 10 includes a non-extensible strap 16 and an inflatable balloon 18, made of a medical grade silicone polymer or any other suitable material, is carried by the inner surface 20 of the strap 16. The balloon 18 may be secured to the inner surface 20 in any well known manner, or even made of unitary construction with the strap 16, although the strap 16 may typically be formed of a different material.

One end of a flexible conduit 22 is in fluid communication with the internal cavity 24 of the balloon 18, with the other end being in fluid communication with an internal cavity (not shown) of a remote injection port 26. The remote injection port 26 includes a silicone septum 28. At the time the adjustable gastric band 10 is implanted around a portion of the stomach, the remote injection port 26 is also implanted at a suitable location, usually within the rectus sheaths, for transcutaneous access via a Huber needle.

As is well known, the internal cavity 24, the flexible conduit 22 and the internal cavity of the remote injection port 26 are preferably at least partially filled with a physiologically compatible fluid, such as a saline solution. Postoperative adjustment of the perimeter enclosed by the balloon 18, and therefore the size of the stoma, is accomplished by addition or removal of fluid from the interior cavity 24 of the balloon 18 by inserting a Huber needle percutaneously into the silicone septum 28 of the injection port 18.

As is well known in the field the adjustable gastric band 10 may be made from any suitable medically compatible material having sufficient strength necessary for a particular laparoscopic surgery or particular patient.

As mentioned above, the two ends of the adjustable gastric band 10 are attached together (the specific attachment mechanism structure is not illustrated in FIG. 1). The present invention is directed to various embodiments of attachment mechanisms for connecting the two ends together in which there are two steps required to attach the ends together. The general construction of adjustable gastric band 10 shown in FIGS. 1 and 2 and described above is common to the embodiments illustrated in FIGS. 3-14, with the embodiments differing by the specific attachment mechanisms. It is noted that the practice of the present invention may be used with any band, and is not limited to use with an adjustable gastric band having the exact features described above or below.

Turning now to FIG. 3, the adjustable gastric band 30 includes an elongated strap 32 extending in what is referred to herein as the longitudinal direction, even though when implanted the adjustable gastric band 30 has an arcuate configuration. The strap 32 includes an inner surface 34 and an outer surface 36, with the balloon 38 extending inwardly from adjacent the inner surface 34. The adjustable gastric band 30 includes a first end portion 40 which overlaps a second end portion 42, with the inner surface 34 of the adjustable gastric band 30 at the first end portion 40 being disposed adjacent and outside the outer surface 36 of the adjustable gastric band 30 at the second end 42 portion.

Referring also to FIG. 4A, the first and second end portions 40, 42 are secured together by a two step attachment mechanism. The first end portion 40 of the strap 32 terminates in an elongated member 44. The elongated member 44 includes a doughnut-shaped enlarged portion 46, having an opening 48 formed therethrough. The enlarged portion 46 has cutouts 50 configured to allow an instrument to grasp the enlarged portion 46 to maneuver it as needed.

The elongated member 44 includes two enlarged, spaced apart spherical portions 52a, 52b disposed at the distal end of elongated member 46, in a barbell configuration, with a portions 44a, 44b of elongated member 44 extending between spherical portions 52a and 52b, and between spherical portion 52b and enlarged portion 46, respectively. It will be appreciated that portions 52a and 52b are not limited to a spherical shape, and may be any suitable shape.

Extending from the outer surface 36 of the second end portion 42 of the strap 32 is at least one laterally extending member 54 which is configured to engage the first end portion 40. The laterally extending member 54 defines a passageway 56, also referred to herein as an opening, through which the first end portion 40 is configured to extend in a longitudinal direction. The passageway 56 has a cross sectional shape and size which is complementary to the cross sectional shape and size of the elongated member 44. At least one dimension of the passageway 56 is smaller than the corresponding dimension of the enlarged portion 46, and in the depicted embodiment, the passageway 56 is smaller in both height and width. The passageway 56 is also depicted as being smaller in both height and width than the spherical portions 52a and 52b, although the passageway 56 may alternatively be large enough for portions 52a and 52b to pass therethrough without any resistance.

The distal end of the second end portion 42 has two spaced apart tabs 58, 60 having angled surfaces 58a, 60a and transverse surfaces 58b, 60b, which together form a notch 62 when viewed from above. The first end portion 40 includes corresponding surfaces 64a, 64b, 66a and 66b which are shaped complementarily to and engage notch 62 when the two end portions 40, 42 are engaged, as described below. The second end portion 42 also includes an opening or recess 68 formed in the outer surface 36. The recess 68 is shaped complementary to and receives the spherical end portion 52a, as described below.

The first step in engaging the two step attachment mechanism together is to activate the first latching mechanism to attach the first end portion 40 to the second end portion 42, by pulling the elongated member 44, including the spherical portions 52a, 52b and the enlarged portion 46 through the passageway 56. Although the dimensions of the passageway 56 relative to the portions 44a, 44b and the spherical portions 52a, 52b may allow the distal end of the elongated member 44 to be pushed through the passageway 56, in the embodiment depicted, the distal end of the elongated member 44 is pulled through the passageway 56 using an instrument, such as a grasper, to engage at least the spherical portion 52a.

Referring to FIG. 4B, the spherical portions 52a, 52b have been pulled completely through the passageway 56, with the enlarged portion 46 still partially disposed therein. As shown, the enlarged portion 46 and the lateral member 54 elastically deform during this first step.

FIG. 4C illustrates the configuration of the two step attachment mechanism in-between the first and second steps of the engagement process, with the enlarged portion 46 having been pulled almost completely through the passageway 56, and the surfaces 64a, 64b, 66a and 66b urged into engagement with the notch 62 to provide transverse stability. With the first latching mechanism so activated by the first step, the final circumferential size/diameter of the band has been established. Alternatively, the length of portion 44c of the elongated member 44 may be sized such that the enlarged portion 46 is completely outside of the passageway 56, although preferably the surfaces 64a, 64b, 66a and 66b are urged into engagement with the notch 62.

The second step of engaging the two step attachment mechanism together is to activate the second latching mechanism to maintain the first end portion 40 attached to the second end portion 42, as a back up to the first latching mechanism, in the event of a failure of the first latching mechanism, either by engagement with the second end portion 42, or, as shown in this embodiment, with the first end portion 40. Referring to FIGS. 4C, 4D and 5, the spherical portion 52a is inserted through opening 48 into the position shown in FIGS. 4D and 5, with respective parts of the spherical portions 52a, 52b extending past the upper and lower surfaces 46a, 46b, with part of the spherical portion 52a disposed in the recess 68. The opening 48 is sized such that, in combination with the elasticity of the enlarged portion 46, the spherical portions 52a, 52b are retained in the position shown in FIG. 5. Thus, the spherical portions 52a, 52b and portion 44a comprise a retaining part of the first end portion 40 which cooperates with and engages another part of the first end portion 40, the opening 48. It is noted that portion 44a may be disposed in a variety of positions, including at or near midway between upper and lower surfaces 46a and 46b.

In the embodiment depicted in FIG. 5, the size of the enlarged portion 46 relative to the passageway 56 may be sufficient to retain the band, with the second integral latching mechanism functioning as a back up. The second latching mechanism resists disengagement of the two end portions 40, 42 due to a longitudinal force by the lateral orientation of the retaining part of the first end portion 40.

Figure 6:
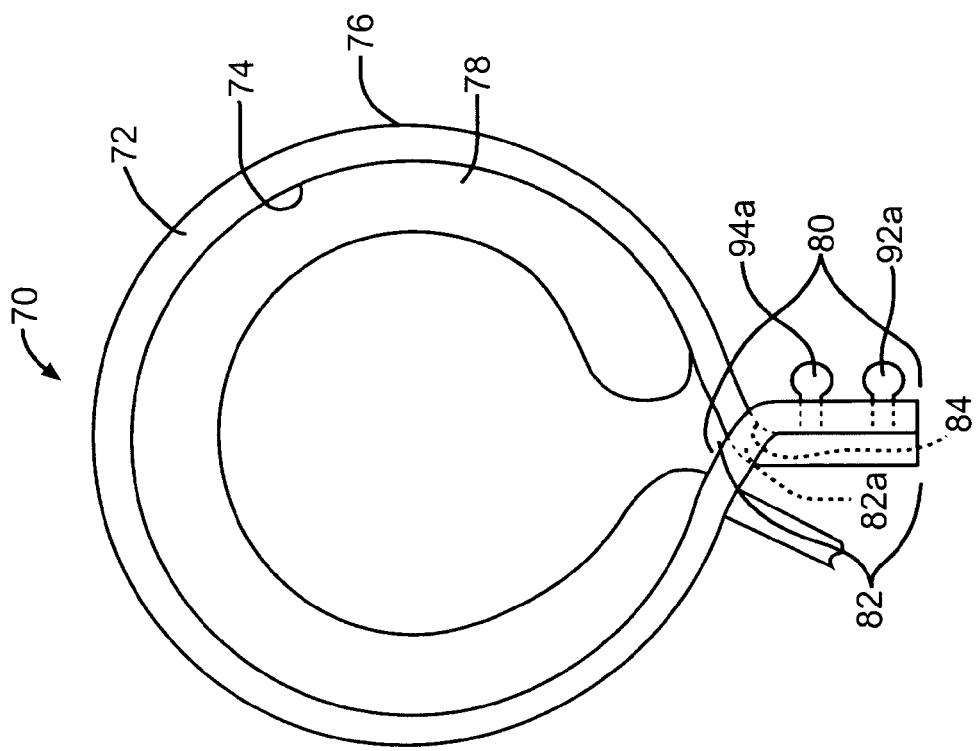
FIG. 6 is a top plan view of another embodiment of an adjustable gastric band constructed in accordance with the present invention having a two step attachment mechanism.

FIG. 6 illustrates another embodiment of an adjustable gastric band having a two step attachment mechanism. The adjustable gastric band 70 includes an elongated strap 72 having an inner surface 74 and an outer surface 76, with the balloon 78 extending inwardly. The adjustable gastric band 70 includes a first end portion 80 which overlaps a second end portion 82, with the outer surface 76 at the first end portion 80 being disposed adjacent the outer surface 76 at the second end 82 portion.

Figure 7:
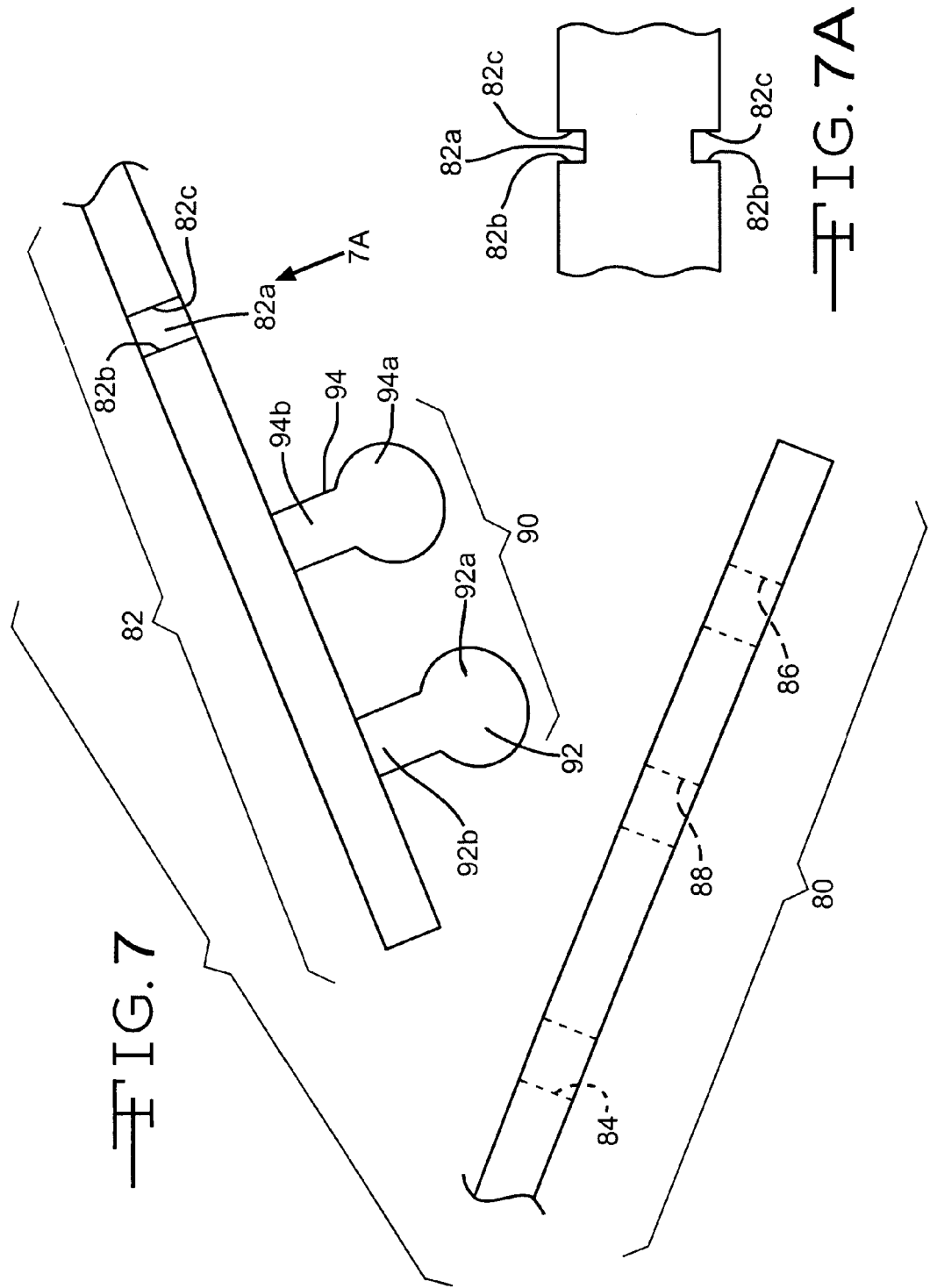
FIG. 7 is an enlarged, fragmentary top view of the two step attachment mechanism shown in FIG. 6, in an unengaged condition.

Referring also to FIG. 7, which illustrates the first and second end portions 80, 82 in an unengaged condition, the first end portion 80 includes a lateral passageway 84, also referred to herein as an opening, which is configured to have the second end portion 82 inserted therethrough. The first end portion 80 also includes two lateral openings 86, 88. The second end portion 82 includes a retaining part 90 comprising the two spaced apart laterally extending members 92, 94 each having an enlarged portion 92a, 94a at the respective distal ends. The two lateral openings 86, 88 are sized and shaped to cooperate with the members 92, 94, retaining them after the enlarged portions 92a, 94a have been pushed through, as seen in FIG. 6.

The transverse dimension of the second end portion 82 which extends beyond the lateral passageway 84 may be larger than the corresponding transverse dimension of the lateral passageway 84. To achieve this, the second end portion may be notched, having a neck portion 82a with a reduced transverse dimension which is approximately the same as the transverse dimension of the lateral passageway 84. In this configuration, at either end of the neck portion 82a there are spaced apart generally transversely extending surfaces 82b and 82c. Alternatively, the transverse dimension of the second end portion 82 may be constant along its length, approximately the same as the lateral dimension of the lateral passageway 84. Or, the second end portion 82 could have two or more transverse dimensions, stepping up at surface 82b (with no corresponding surface 82c) from a transverse dimension which is approximately the transverse width of the lateral passageway 84 to a transverse dimension greater than the transverse dimension of the lateral passageway 84

The first step in engaging the two end portions 80, 82, is activating the first latching mechanism by inserting the second end portion 82 through the opening 84, past the lateral member 94, until the neck portion 82a extends through the lateral passageway 84, with the surfaces 82b adjacent the outer surface 76 of first end portion 80. With the first latching mechanism so activated by the first step, the final circumferential size/diameter of the band has been established. The surfaces 82b and 82c preclude significant movement between the first and second end portions 80, 82 following the first step. The surfaces 82b are important in this configuration of this embodiment to establish the maximum final diameter, and the surfaces 82c may be omitted or located further away from the surfaces 82b without affecting this.

The second step is activating the second latching mechanism by engaging the retaining part 90 with the first end portion 80, inserting the members 92, 94 into the respective openings 86, 88, further retaining the first end portion 80 in place, backing up the first latching mechanism, such as in the event it fails, completely or partially. As will be appreciated, one or more than two lateral members and corresponding cooperating openings may be used, as well as different shapes which cooperate together to remain in engagement.

Figure 8:
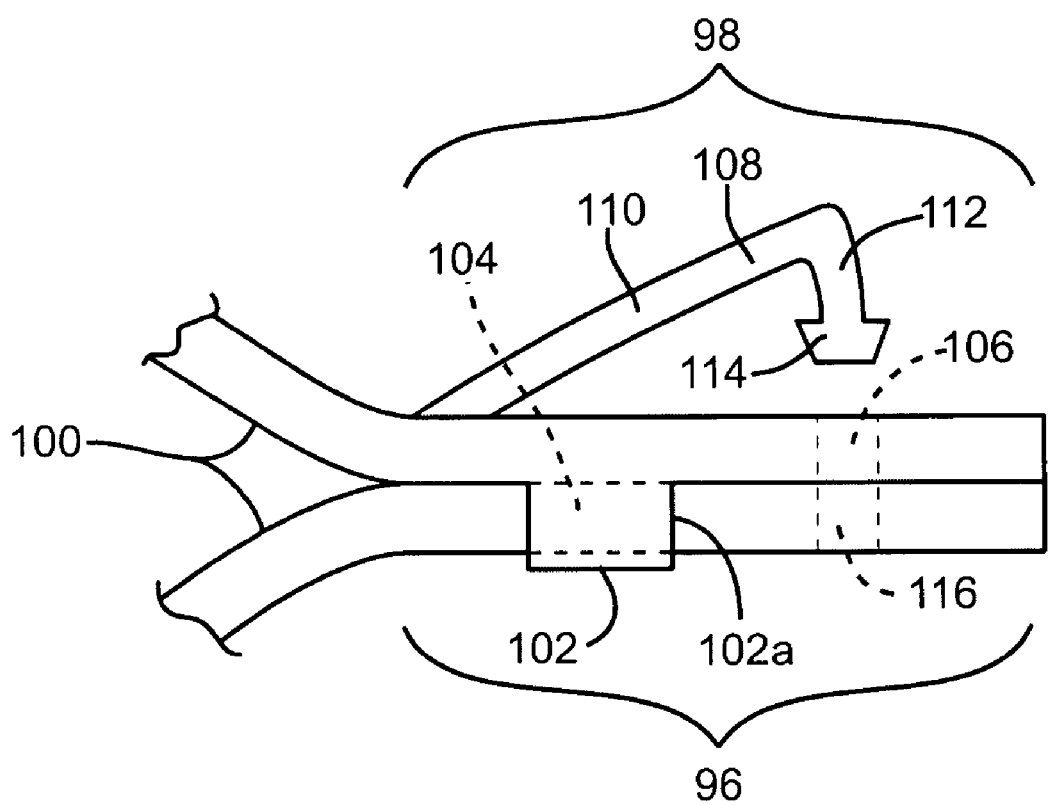
FIG. 8 is an enlarged, fragmentary top view of another embodiment of a two step attachment mechanism constructed in accordance with the present invention.

FIG. 8 illustrates another embodiment of an adjustable gastric band having a two step attachment mechanism. In FIG. 8, only the first and second end portions 96, 98 are illustrated engaged together, with the inner surface 100 at the first end portion 96 being disposed adjacent the inner surface 100 at the second end 98 portion. The second end portion 98 includes at least one laterally extending member 102 which is configured to engage the first end portion 96. The laterally extending member 102 defines a passageway 104, also referred to as an opening, through which the first end portion 96 is configured to extend in a longitudinal direction.

The second end portion 98 includes a lateral opening 106 and a retaining member 108. Retaining member 108, as depicted, is of unitary construction with second end portion 98, although it could be formed separately and attached in any suitable manner. The distal end of the retaining member 108 includes an arm 110 which terminates in a member or pin 112 having a flared tip 114. The arm 110 and its connection to the second end portion 98 allows the arm to be rotated to move the pin 112 into alignment with and through the opening 106. The connection between the arm 110 and the second end portion 98 may be configured in any manner suitable for the arm 110 to be rotated as described, including for example a living hinge.

The first end portion 96 is sized to extend through the passageway 104 in the longitudinal direction as shown. The first end portion also includes a lateral opening 116.

The first step in engaging the two end portions 96, 98, is inserting the second end portion 96 through the opening 104, to a position at which the opening 116 is aligned with the opening 106. The second step is retaining the first end portion 96 in place by moving the retaining member 108 to advance the pin 112 into the openings 106, 116, such that the large (relative to opening 116) flared tip 114 keeps the pin 112 from backing out of the openings 116 and concomitantly 106.

Alternatively, the retaining member 108 could carried by the first end portion 96 extending over the member 102 to extend through the openings 116, 106 with the flared tip 114 sized to keep the pin 112 from backing out of the opening 106 and concomitantly 116. Also, the opening 106 could be omitted by shortening the second end portion 98 to clear the pin 112 and flared tip 114. A plurality of longitudinally spaced openings formed in the end portion not carrying the retaining member 108 may be used to adjustable sizing of the adjustable gastric band.

Additionally, a portion of the first end portion 96 could have an increased transverse dimension larger than the transverse dimension of the opening 104, forming a step which abuts the end 102a of the laterally extending member 102. In such a configuration, the first step activates the first latching mechanism formed by the cooperation of such steps and the end 102a, establishing the final circumferential size/diameter of the band. The second step, which backs up the first latching mechanism.

Figure 9A:
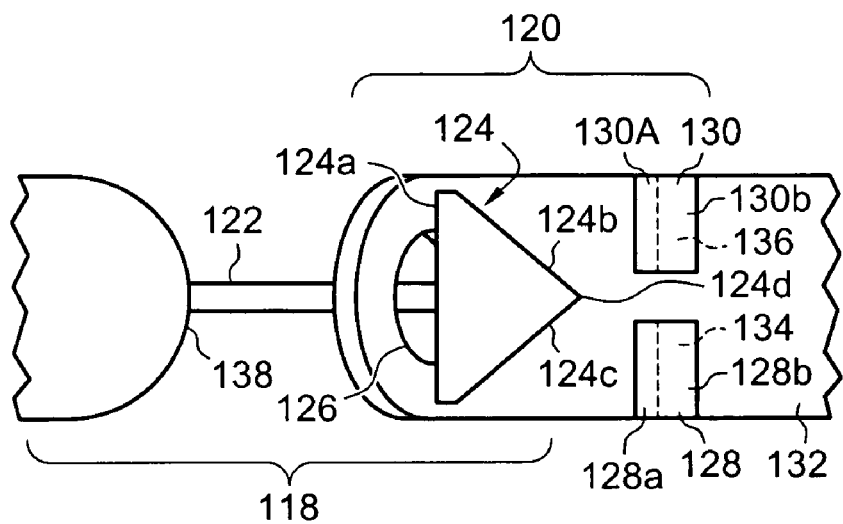
FIGS. 9A & 9B are a sequence of fragmentary top views of another embodiment of a two step attachment mechanism constructed in accordance with the present invention, illustrating the steps in securing the ends together.
Figure 9B:
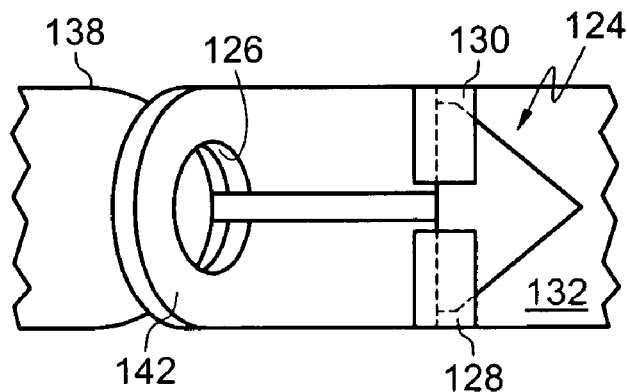
Figure 10:
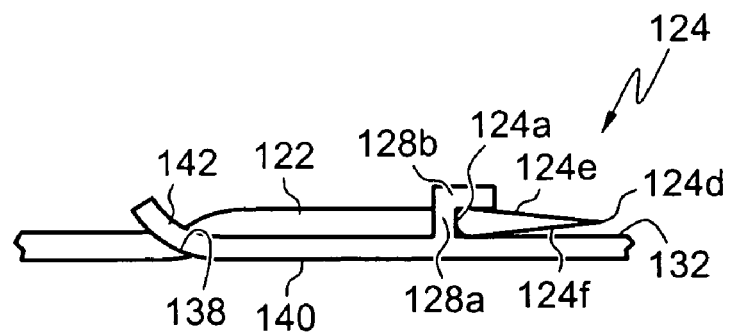
FIG. 10 is a side view of the adjustable gastric band as shown in FIG. 9B.

FIGS. 9A, 9B and 10 illustrate another embodiment of an adjustable gastric band having a two step attachment mechanism. In FIG. 9A only the first and second end portions 118, 120 are illustrated, partially engaged following the first attachment step. The first end portion 118 includes an elongated member 122 which terminates in a retaining part 124 having an arrowhead shape with a wide base 124a from which the leading edges 124b, 124c extend longitudinally to converge at the narrow tip 124d. As seen in FIG. 10, the base 124a has an arcuate lateral profile, from which surfaces 124e, 124f extend to converge at tip 124d. Although first end portion 118 is illustrated as arcuate where member 122 extends, it may be any suitable shape.

Second end 120 includes an opening 126 formed at its distal end, and a pair of spaced apart laterally extending members 128, 130, spaced down from the opening 126. Each laterally extending member 128, 130 includes a laterally extending portion 128a, 130a, connected to a longitudinally extending member 128b, which cooperate with the upper surface 132 of the adjustable gastric band to create an opening 134, 136. The openings 134, 136 are configured to retain the base 124a of retaining part 124, which may include the portions 128b, 130b having lower surfaces inclined toward the outer surface 132.

The first step in engaging the two end portions 118, 120, is inserting the first end portion 118 through the opening 126, advancing it until the edge 138 is urged into contact with the lower surface 140 of the second end portion 120 adjacent the opening 126, with the distal end 142 of second end portion 120 being bent up slightly, as seen in FIG. 10. The second step is retaining the first end portion in place by engaging the retaining part 124 with the second end portion 120, inserting the retaining part 124 into the respective openings 134, 136, locating the base 124a as shown in FIG. 10. The length of member 122 urges distal end 142 toward the bent position shown.

It is noted that retaining part 124 is not limited to an arrowhead shape, and any shape which may be inserted through an opening in the second end portion and function as a retaining member may be used.

Figure 11:
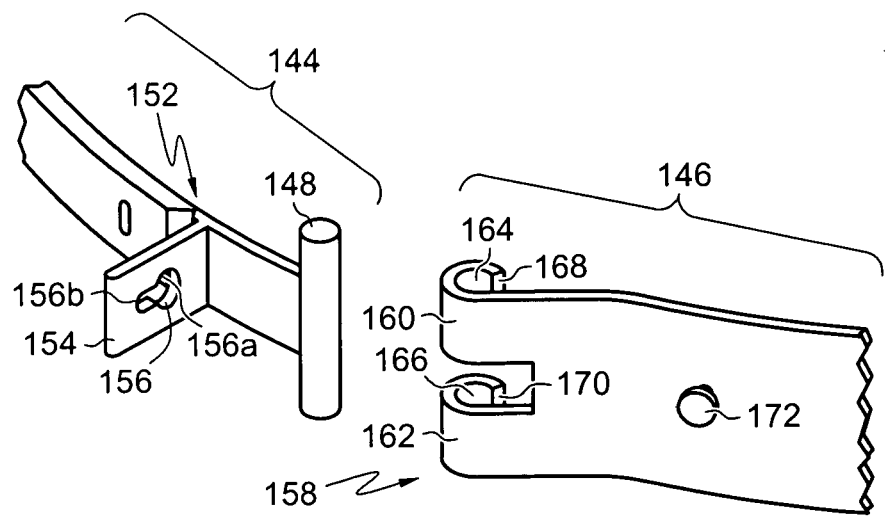
FIG. 11 is an enlarged, fragmentary perspective view of another embodiment of a two step attachment mechanism constructed in accordance with the present invention

FIG. 11 illustrates another embodiment of an adjustable gastric band having a two step attachment mechanism. In FIG. 11, only the first and second end portions 144, 146 are illustrated, disengaged. First end portion 144 terminates in a transversely extending member 148 connected to the rest of the first end portion 144 by a strap 150 through a living hinge 152. A retaining part 154 extends from the strap portion 150, angled away from the member 148, as shown in FIG. 11. The retaining part 154 includes a key hole shaped opening 156.

Figure 12A:
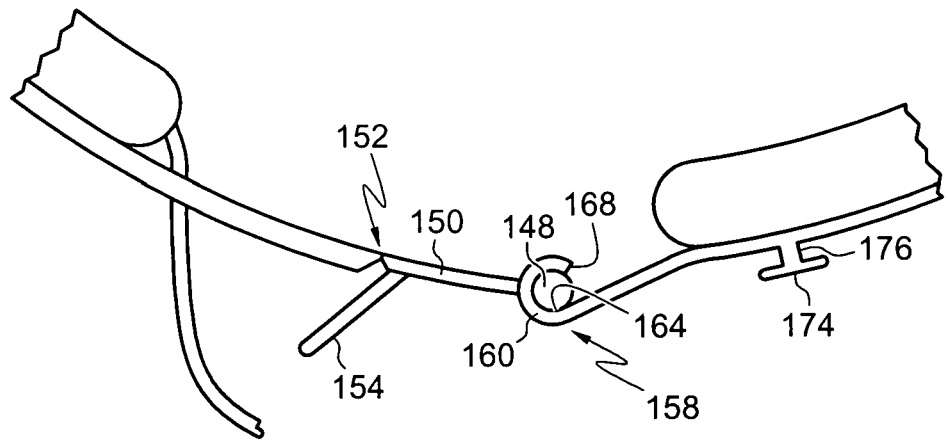
FIGS. 12A & 12B are a sequence of fragmentary top views of the embodiment shown in FIG. 11, illustrating the steps in securing the ends together.
Figure 12B:
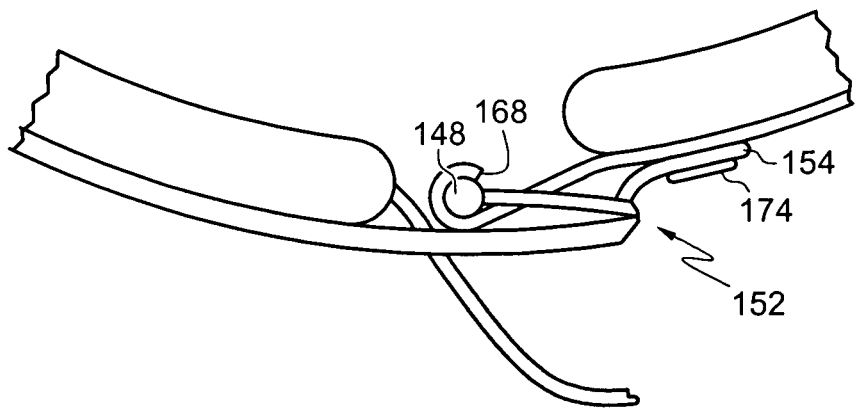

The distal end 158 of the second end portion 146 includes two longitudinally extending spaced apart members 160, 162 which define two spaced apart, aligned openings 164, 166. As seen in FIG. 12A, the openings 164, 166, are shaped complementarily to the member 148 to rotatably receive the member 148, having respective entrance edges 168, 170 which have smaller dimensions than the corresponding dimensions of the member 148.

The second end portion 146 includes a laterally extending member 172, depicted in the shape of a rivet, having a head 174 which is larger than the base 176. Member 172 and opening 156 are configured to cooperate together.

Referring to FIG. 12A, the first step in engaging the two end portions 144, 146, is inserting member 148 into openings 164, 166, which may be done by disposing the member 148 adjacent the entrance edges 168, 170 and applying a longitudinal force sufficient to expand the entrance temporarily until member 148 snaps into place. FIG. 12A illustrates the two step attachment mechanism between the first a The second step is engaging the retaining part 154 with the second end portion 172. The cylindrical member 148 is rotated within openings 164, 166 by moving the retaining part 154 toward the second end portion 146, causing the strap 150 to pivot about the living hinge 152. The head 174 is inserted through the large part 156a of the opening 156, and the base 176 is slide into the small part 156b, thereby retaining the retaining part 154.

Figure 13:
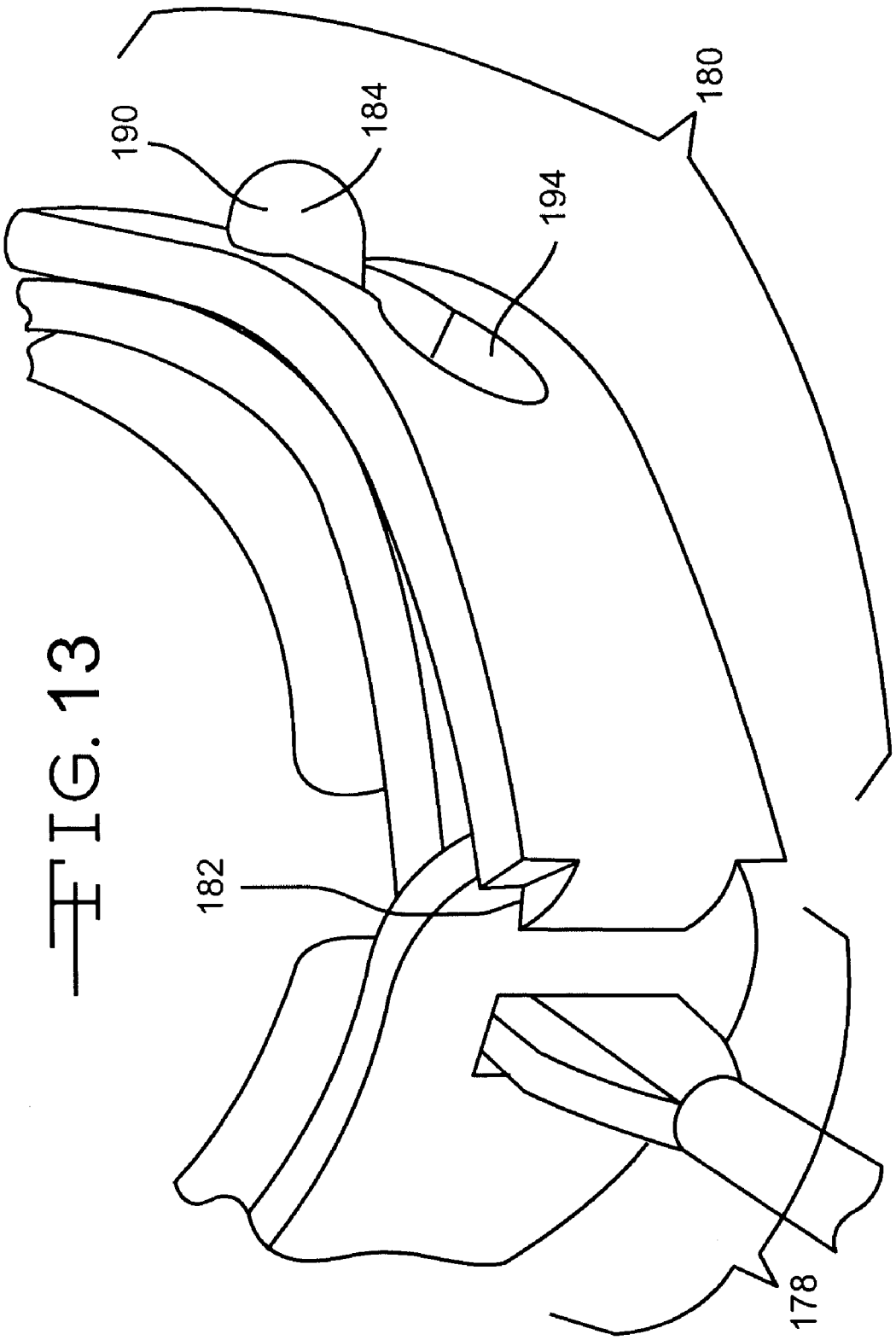
FIG. 13 is an enlarged, fragmentary perspective view of another embodiment of a two step attachment mechanism constructed in accordance with the teachings of the present invention, with the two end portions engaged.

FIGS. 13, 14 and 15 illustrate another embodiment of an adjustable gastric band having a two step attachment mechanism. In FIGS. 13-15, only the first and second end portions 178, 180 are illustrated. The first end portion 178 includes a lateral passageway 182, also referred to herein as an opening, which is configured to have the second end portion 180 inserted therethrough. The second end portion 180 includes a retaining part 184 comprising a member 186 extending laterally from the outer surface 188. The stem member 186 includes an enlarged head portion 190 at its distal end.

Second end portion 180 includes a lateral opening 192 spaced from the retaining part 184 toward the end 180a. In the illustration, the opening 192 has a key way shape with an enlarged portion 194 having a generally circular shape and an elongate slot portion 196 extending in a longitudinal direction. The portion 194 is shaped complementarily to the head portion 190, configured to allow the head portion 190 to be inserted easily therethrough.

Figure 17:
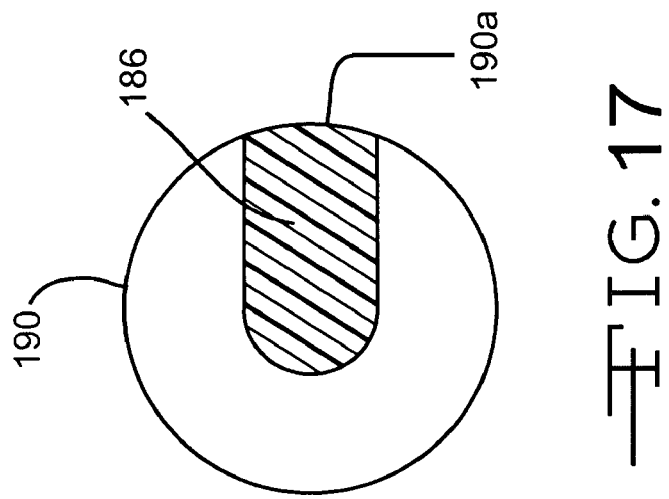
FIG. 17 is a cross-sectional view of the retaining part of FIG. 14, taken along line 17-17 of FIG. 16.
Figure 16:
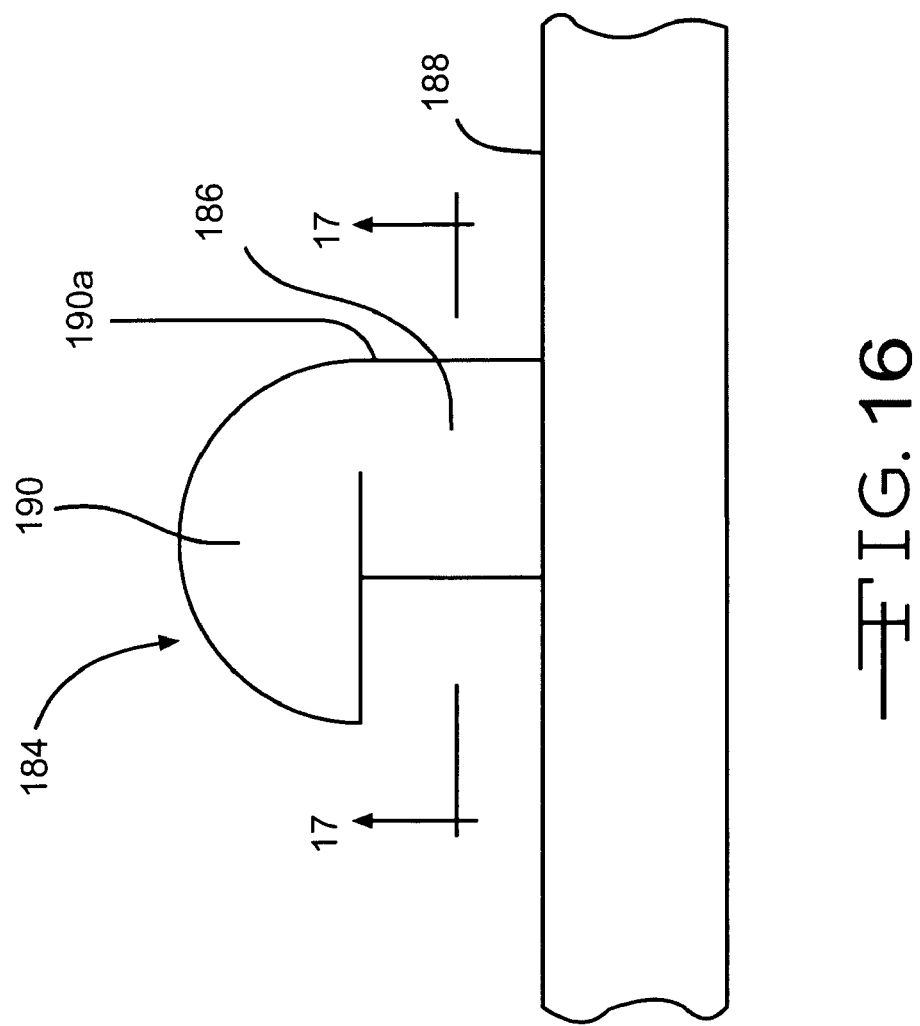
FIG. 16 is a partial side view of the retaining part of FIG. 14.

The slot 192 is shaped complementary to stem member 186. As seen in FIGS. 16 and 17, member 186 extends in the longitudinal direction, having a transverse dimension which is complementary to the transverse dimension of the slot 192. In the embodiment depicted, the stem member 186 extends from the edge 190a of the head portion 190 to past the center of the head portion 190.

The second end portion 180 past is notched between retaining member 184 and opening 192, having a neck portion 198 with a reduced transverse dimension which is approximately the same as the transverse dimension of the lateral passageway 182. In this configuration, at either end of the neck portion 196, there are spaced apart generally transversely extending surfaces 200, 202. Alternatively, the transverse dimension of the second end portion 180 may be constant along its length, approximately the same as the lateral dimension of the lateral passageway 182. Or, the second end portion 180 could have two or more transverse dimensions, stepping up at surface 202 (with no corresponding surface 200) from a transverse dimension which is approximately the transverse width of the lateral passageway 182 to a transverse dimension greater than the transverse dimension of the lateral passageway 182.

The longitudinal dimension between the notch centerline between surfaces 200 and 202 and the centerline of retaining member 184 is approximately equal to the longitudinal dimension between the notch centerline and the center of the semicircular end 196a.

Referring to FIG. 13, the first step in engaging the two end portions 178, 180, is activating the first latching mechanism by inserting the second end portion 180 through the opening 182, past the retaining member 184, until the neck portion 194 is disposed in the opening 182. With the first latching mechanism so activated by the first step, the final circumferential size/diameter of the band has been established. The surfaces 200 and 202 preclude significant movement between the fist and second end portions 178, 180.

The second step is activating the second latching mechanism by inserting the retaining part 184 into the opening 192. The head portion 190 is inserted into the portion 194 by pulling the end 180a to align the two. The tension on the second end portion 180 past the neck, or hinge portion, 194, causes the stem member 186 to move into the slot portion 186 to abut end 196a. The tension is the result of the approximately equal respective dimensions between the centerline of the retaining member 184, the neck, or hinge portion, 194, and the centerline of the end 196a. The second step backs up the first latching mechanism.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

Thus, as used herein and in the claims, an implantable band is a band which may be implanted in a position to occlude flow, such as food or body fluids, through an anatomical passageway, such as a stomach or lumen.

In summary, numerous benefits have been described which result from employing the concepts of the invention. The foregoing description of one or more embodiments of the invention has been presented for purposes of illustration and description. It is not intended to be exhaustive or to limit the invention to the precise form disclosed. Obvious modifications or variations are possible in light of the above teachings. The one or more embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. An implantable band for treatment of a medical condition, the band comprising:
 (a) a strap configured to encircle an anatomical passageway, said strap defining a circumferential direction thereabout, said strap having an inner and outer surface;

(b) first and second end portions disposed at either end of said strap, said first and second end portions configured to be attached to each other so as to secure said strap adjacent the anatomical passageway, said first and second end portions including respective inner and outer surfaces which correspond to said inner and outer surfaces of said strap, said second end portion comprising a barb head having a base and a tip, wherein base is wider than the tip;

(c) said first end portion including opening defining portion, wherein the opening defining portion defines at least one first opening configured to receive part of said second end portion therein, said part of said second end portion being configured to be disposed in said at least one first opening, wherein the barb head is configured to pass through the first opening, wherein the opening defining portion terminates at a first longitudinal position along the first end portion and at a second longitudinal position along the first end portion;

(d) said first end portion including a retaining part, said retaining part being configured to connect to said second end portion at an engagement point, wherein the engagement point is located at a third longitudinal position along the first end portion, wherein the third longitudinal position is longitudinally displaced from the first and second longitudinal positions, the retaining part being configured so as to resist withdrawal of said part of said second end portion from said at least one first opening, wherein said retaining part comprises a lateral member extending laterally from said first end portion, said lateral member being configured to engage the base of the barb head at the engagement point wherein the second end portion is secured to the first end portion, such that the base of the barb head is engaged with the lateral member at the engagement point and the part of said second end portion is disposed in said at least one first opening.

2. The band of claim 1, wherein said barb head includes an enlarged portion which has a transverse dimension that is larger than a corresponding dimension of said first opening.

3. The band of claim 1, wherein said barb head includes an enlarged portion which has height and width dimensions which correspond to dimensions of said first opening such that at least one of said height and width dimensions is larger than the corresponding dimension of said first opening.

4. The band of claim 1, wherein said barb head comprises a flared tip.

5. An implantable band for treatment of a medical condition, the band comprising:
(a) a strap configured to encircle an anatomical passageway, said strap defining a circumferential direction thereabout, said strap having an inner and outer surface;
(b) first and second end portions disposed at either end of said strap, said first and second end portions configured to be attached to each other so as to secure said strap adjacent the anatomical passageway, said first and second end portions including respective inner and outer surfaces which correspond to said inner and outer surfaces of said strap, said second end portion having a fastening member, wherein the fastening member comprises a distal tip region and a rear edge, the second end portion further comprising a distally facing edge located proximal to the fastening member; and
(c) said first end portion including a two step attachment mechanism, wherein the two step attachment mechanism comprises:
(i) an opening defining portion defining at least one first opening configured to receive part of said second end portion therein, said part of said second end portion being configured to be disposed in said at least one first opening, wherein the distally facing edge of the second end portion is configured to engage the opening defining portion of the first end portion when the part of the second end portion is disposed in the at least one first opening, and
(ii) a retaining part, said retaining part being configured to engage the fastening member of said second end portion so as to resist withdrawal of said part of said second end portion from said at least one first opening, wherein said retaining part is longitudinally displaced from said opening defining portion, wherein said retaining part includes at least one lateral member extending laterally from said first end portion, wherein the lateral member is configured to engage the rear edge of the fastening member of the second end when the part of the second end portion is disposed in the at least one first opening;
wherein the first and second end portions are secured together, such that the part of the second end portion is disposed in the at least one first opening and such that the rear edge of the fastening member is engaged with the lateral member.

6. The band of claim 5, wherein said fastening member includes an enlarged portion which has a transverse dimension that is larger than a corresponding dimension of said first opening.

7. The band of claim 5, wherein said fastening member includes an enlarged portion which has height and width dimensions which correspond to dimensions of said first opening such that at least one of said height and width dimensions is larger than the corresponding dimension of said first opening.

8. The band of claim 5, wherein said retaining part includes a first lateral member and a second lateral member.

9. An implantable band for treatment of a medical condition, the band comprising:
(a) a strap configured to encircle an anatomical passageway, the strap having an inner and outer surface;
(b) an inflatable balloon secured to the inner surface of the strap;
(c) a first end portion disposed at a first end of the strap, wherein the first end portion defines an opening; and
(d) a second end portion disposed at a second end of the strap, wherein the second end portion comprises a distally facing edge, a barb head having a proximally facing edge, and an elongate portion extending between the distally facing edge and the barb head, wherein the barb head is distal to the distally facing edge;
wherein the second end portion is coupled with the first end portion such that the strap defines a circumferential perimeter when the second end portion is coupled with the first end portion;
wherein the distally facing edge of the second portion is engaged with the first end portion at a first longitudinal position along the first end portion;
wherein the proximally facing edge of the barb head is engaged with the first end portion at a second longitudinal position along the first end portion;
wherein engagement of the distally facing edge of the second portion with the first end portion restricts movement of the second end portion along a first circumferential direction;
wherein engagement of the proximally facing edge of the barb head with the first end portion restricts movement of the second end portion along a second circumferential direction, opposite to the first circumferential direction.

* * * * *